(12) United States Patent
Kechichian

(10) Patent No.: US 6,906,236 B2
(45) Date of Patent: Jun. 14, 2005

(54) ABSORBENT PRODUCT

(76) Inventor: Missak Kechichian, Imtiergarten 57, 8055 Zurich (CH)

(*) Notice: Subject to any disclaimer, the term of this patent is extended or adjusted under 35 U.S.C. 154(b) by 1 day.

(21) Appl. No.: 10/470,777

(22) PCT Filed: Jan. 31, 2001

(86) PCT No.: PCT/IT01/00047
§ 371 (c)(1),
(2), (4) Date: Dec. 24, 2003

(87) PCT Pub. No.: WO02/060367
PCT Pub. Date: Aug. 8, 2002

(65) Prior Publication Data
US 2004/0087925 A1 May 6, 2004

(51) Int. Cl.$^7$ ................................................. A61F 13/15
(52) U.S. Cl. ........................ 604/367; 604/359; 604/378; 424/76.4; 424/76.5; 424/76.6
(58) Field of Search ................................. 604/368, 367, 604/378, 359; 424/76.1–76.5, 76.6

(56) References Cited

U.S. PATENT DOCUMENTS

| | | | | | |
|---|---|---|---|---|---|
| 5,849,816 | A | * | 12/1998 | Suskind et al. | ............. 523/201 |
| 6,599,989 | B2 | * | 7/2003 | Wada et al. | ............. 525/329.7 |
| 6,667,424 | B1 | * | 12/2003 | Hamilton et al. | ........... 604/375 |
| 2004/0116883 | A1 | * | 6/2004 | Krautkramer et al. | ...... 604/367 |

* cited by examiner

Primary Examiner—Jacqueline F. Stephens
(74) Attorney, Agent, or Firm—Browdy and Neimark, P.L.L.C.

(57) ABSTRACT

An absorbent product (1) comprising a flexible support (2), having a first layer (4) and a second layer (3) of granulated clay material, and a porous fibrous fabric (5) apt to secure said first and second layer (3, 4) on said flexible support (2) arranged at the top thereof.

8 Claims, 3 Drawing Sheets

ABSORBENT PRODUCT

DESCRIPTION

The present invention relates to an absorbent product like a diaper, a sanitary napkin or the like and, more precisely, to an absorbent product containing clay and apt to completely eliminate physiological secretion in a separate and distinct manner.

Current sanitary garments like absorbent products are designed to have a satisfactory functionality based on urine absorption alone, whereas the solid fractions remain on the surface thereof, i.e., in close contact with the wearer body, not warranting nor providing acceptable operational hygienic conditions.

Moreover, further to experimental tests, the present Inventor observed that diapers, as well as currently marketed sanitary napkins, easily get soaked, possibly creating an unhealthy, dirty, health-aggressive and noxious environment. This is caused by the possible concomitant presence of urine and feces in a closed, warm environment, and by the total lack of provision of means for treating, removing and separating feces and urine. In fact, possible blood clots or feces remain deposited onto the garments contacting the skin, exposing the latter to the presence of highly aggressive and harmful bacteria and enzymes, causing even serious illnesses and troubles.

In fact, for manufacturing said diapers or napkins to date natural or synthetic fibrous materials, with some addition of other nonfibrous absorbent material in an attempt to increase the poor absorbing-binding power of the fiber, are used.

Therefore, such products have the main drawback of being unsuitably designed for the physiological needs, not providing any mechanism or way to separate and/or remove feces nor urine.

Moreover, the use of clay as absorbent material for absorbent products in the personal or sanitary hygiene field as a material incorporated in an absorbent product is also known. Actually, it is likewise known that clay has as mineralogical components hydrated aluminosilicates, also containing iron, magnesium, potassium, calcium and sodium, of lamellar structure, known as "clay minerals" like the kaolinite, sericite, and montmorillonite, providing the characteristic properties of clay: plasticity, high binding power and high aqueous fluid absorptive capacity, swelling enormously up to 14 times its own volume.

U.S. Pat. No. 3,935,363 discloses an absorbent product containing flocculated clay mineral aggregates providing a flexible fibrous support in which the abovementioned granulated clay mineral aggregates are dispersed, so as to implement an absorbent product.

According to the abovecited Patent, it is provided that the clay minerals be pre-treated with a flocculating agent like, e.g., small quantities of polymeric materials such as the polyacrylic acid, polystyrene and the like, in order to allow optimum flocculation. Then, after flocculation, the aggregates are filtered to separate them from the aqueous solution and subsequently dried to be incorporated into the fibrous support, thus constructing the absorbent product.

The solution advanced in the abovecited Patent, though effective in enhancing the fluid absorptive power of the end product, has a drawback lying in the need to provide a thorough pretreatment of the clay or of its minerals prior to the use thereof in the absorbent product. This entails an industrial process of treatment and manufacture of clay flocculates, in turn entailing additional costs and complication with respect to the extant absorbent products. Moreover, another drawback thereof lies in that the sanitary products thus obtained are not apt to eliminate the feces by particulation, being merely apt to decrease garment dampness. This entails an unhygienic condition, due to the presence of feces in contact with the body skin, with the related aggressive and injurious effects.

Furthermore, U.S. Pat. No. 5,869,033 discloses a diaper apt to prevent skin irritation from soiled diapers, providing the use of organophilic clay, i.e., clay treated and transformed with organic substances and molecules. However, also in this patent the problem linked to the elimination of feces is not dealt with, therefore the injurious effect on skin persists as aboveillustrated.

Hence, it is an object of the present invention to overcome the abovementioned drawbacks providing a process for the manufacture of an absorbent product foreseeing the use of clay as an extremely effective absorbent material, yet with no need to provide a chemical pretreatment of the former.

Another object of the present invention is to provide an absorbent product incorporating clay that be apt to absorb urine and likewise effective in absorbing and eliminating the feces, thereby avoiding possible skin irritation and ensuring an elevated level of hygiene.

A further object of the present invention is to provide an absorbent product incorporating clay that be simple to manufacture and above all inexpensive, particularly apt to be used as sanitary absorbent product for human use and with absorbent, anallergic and antiinflammatory properties.

Hence, the present invention provides an absorbent product according to claim 1.

A detailed description of several preferred embodiments of the present invention, given by way of example and not for limitative purposes, will hereinafter be disclosed, making reference to the annexed drawings, wherein.

Figure 5:
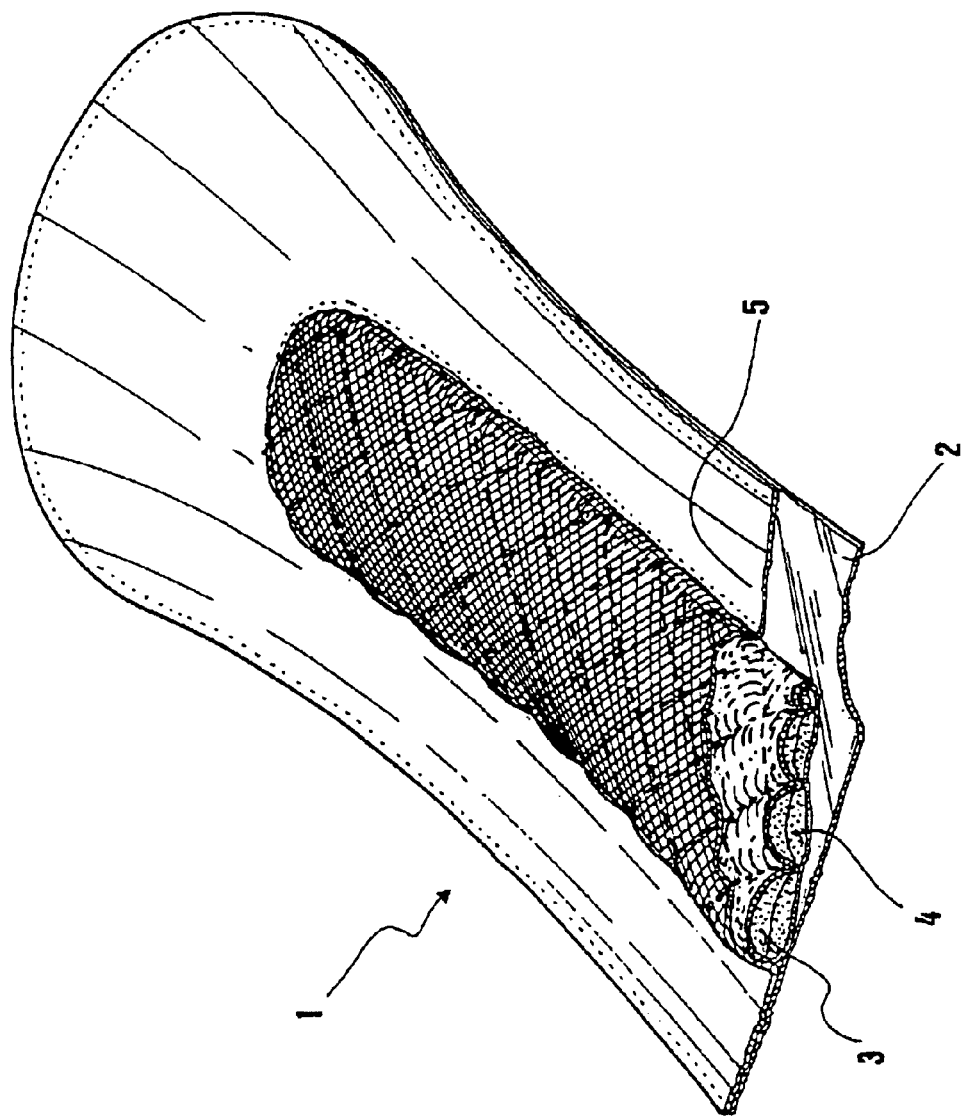
FIG. 5 shows in a partial section view the sanitary absorbent product obtained according to a first embodiment of the present invention.

With reference now to FIG. 5, the absorbent product according to an embodiment of the present invention will be illustrated. According to the invention, it is provided a sanitary absorbent product 1, such as a diaper or the like, providing a flexible support 2 made of a conventional water impermeable non woven fabric. At the central area of the support 2, two differentiated and separated layers of absorbent material made of granulated clay of different granulometry, 3 and 4, respectively, are arranged, as it will be better illustrated hereinafter.

The first layer 3 is made of a band of granulated clay material of preset granulometry and dedicated to the elimination of the feces, whereas the underlying band or layer 4 is dedicated to the elimination of the urine and is made of clay having a smaller granulometry with respect to that of the layer 3. The fabric thus assembled is secured onto the flexible support 2 with the application of a porous or substantially reticulated fabric web 5 arranged onto the top layer 3 and onto the support 2 in a <<materassé>> arrangement apt to secure each layer 3 and 4 onto the support in a substantially homogeneous distribution even during use. The fabric web 5 has a permeability allowing the passage of body fluids, yet not outletting clay material particulate.

The crucial concept of elimination of solid (feces or blood clots) and of liquid (urine and/or blood) particles according to the present invention shall hereinafter be made apparent.

In order to be eliminated, the liquids are first absorbed on the surface, then seeping in depth into the clay granules; whereas the solids need to undergo a series of state transformations, being mechanically particulated to be absorbed, bound and aggregated to the clay. Therefore, according to the fabric of the present invention, by 'elimination' it is not meant the mere absorption of liquids and/or the deposit of solids onto an absorbent support, but the outcome of a series of transformation steps or stages. Hence, with the fabric of the present invention, the granulated clay allows to attain three fundamental aims:

a) eliminating the urine and the feces by absorption via the pores of the porous granulated clay;

b) implementing the direct skin-granulated clay contact; and c) attaining an effective feces/liquid division The porous granulated layer offers a wide useful surface to the absorption of the liquid component, concomitantly providing, due to the friction between adjacent granules of the same granulated clay material, the possibility of dividing the feces. The selection of porous granulated clay for use is due to the fact that it behaves as a microcollector with liquids, conveying the latter corewise each granule, whereas the solid particles are absorbed onto the porous surface of the granules and then being finally removed by a concomitant chemico-mechanical action.

For a selection of the granulation, the following aspects should be taken into account. An exceedingly coarse granulation would be bulky and rather impractical, whereas an exceedingly fine granulation might cause a colloidal situation, given the aptness of clay to create colloidal suspensions. On the other hand, an excessive quantity of clay generates bulkiness and weight-related problems. Therefore, the following factors should be evaluated: clay quantity, clay granulometry, quantity of urine and feces. These factors should be examined and studied together, and set within certain boundaries of convenience. The quantity of urine and feces is generally set within certain boundaries on the basis both of the physiological function and of the age. The clay granulometry and quantity should follow this standard. Hence, it is considered an appropriate compromise between the quantity and the granulometry when the individual grain attains the approximate dimensions of 5 mm Ø, whereas the total weight should range from 200 to a maximum of 300 gr., in order to make the absorbent product practical and less bulky.

Figure 1:
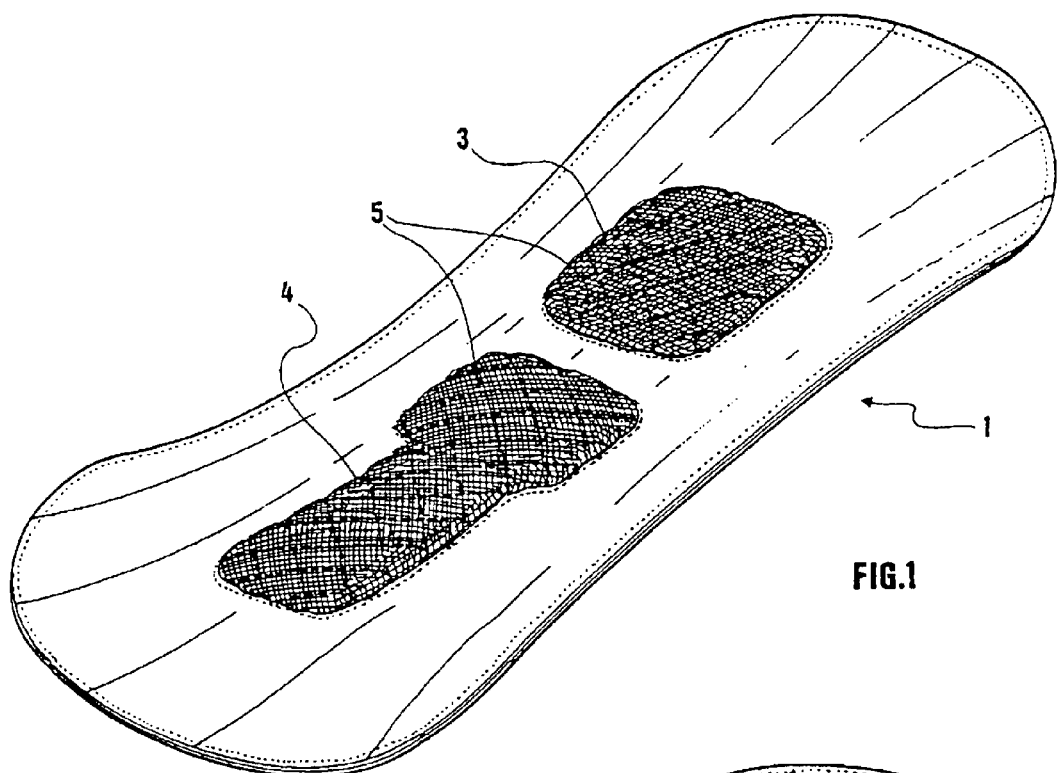
FIG. 1 shows a sanitary absorbent product obtained according to a first embodiment of the present invention.

With reference now to FIG. 1, an absorbent product, apt to make a diaper 1 for infants improved so as to provide its function, essential to the hygiene and well-being of the infant, and being useful to eliminate the urine and the feces concomitantly protecting the infant body from possible irritation, is illustrated.

For the sake of clarity, same parts will hereinafter be indicated by the same reference numbers.

For the implementation of the diaper 1 a flexible support 2 is provided, onto which, at the central area thereof, a certain preset and ready for use quantity of granulated clay is arranged. The dimensions of the support 2 suffice to wrap an infant. The clay is circularly spread onto the support 2, thus forming a first pad 3 for the feces of a 10–15 cm size and at the area housing the infant buttock. Concomitantly, a second urine pad 4 is formed, at the front of the infant body and substantially T-shaped, thereby being particularly suitable for both sexes.

Then, the pad 3 and 4 thus obtained are made integral to the support 2 by the fabric web 5, in order to avoid any clay discharge.

The operation of the diaper according to the present invention will hereinafter be considered.

Urine Absorption.

For 'absorption' the retaining of the urine, initially onto the surface portion of the clay granules and subsequently to be percolated corewise thereto, being bound by chemico-physical forces and thus finally generating stable liquids or granules, is meant. I.e., the spouted urine collides with the porous granulated clay, easily seeping among the granules, thereby being absorbed by the innermost portion thereof while leaving unsoiled and dry the outermost skin-contacting portion thereof.

Elimination of Feces.

It has to be pointed out that the actual fecal consistency depends on the diet, age and physical condition of the infant. The feces of breast-fed babies have a fluid and pasty consistency, whereas those of bottle-fed babies are denser and bulkier. For the sake of simplicity, only three particular and specific cases of fecal consistency will be considered here, epitomizing any real situation:

fluid feces;

pasty feces;

solid feces.

Fluid Feces.

Definitely, this is the most favourable and effective situation for eliminating the feces. The fluid fecal flow gushes out when expelled, thereby allowing the mass to flow, penetrate and disperse among the clay granules, expanding widthwise and depthwise thereamong. The fluid and liquid fraction is readily absorbed by the granulated clay and instantly removed. The particles, already divided and wetted, are easily absorbed and bound by the wide granular surface which is available by virtue of the porosity of the clay, and permanently fixed therein.

In this case, the strength required for the supporting thereof is minimal; the fecal particles, being almost completely divided and dispersed into the fluid means, are easily carried in depth and dispersed by the latter. The absorption of the fecal particles is near-spontaneous, requiring little energy and mechanisms.

Pasty Feces

Pasty feces, by virtue of the expelling force, meet the clay granules undergoing a first separation and division. However, the actual particulation takes place by virtue of the natural motion of the body and legs, which generate the force required to divide the feces pushing the latter in depth through the porous fabric 5. In fact, the feces synergistically act with the available body forces as a mechanical means, carrying out the division and overcoming friction to transform the mass into several particles. As formed, the latter being still damp easily adhere to the granulated porous clay surface, and are subjected to continual tiny shiftings by the body motion which suffice to bring new unsoiled granules into contact therewith. Once dispersion and particulation are attained, the remainder proceeds as disclosed in the case of fluid feces, i.e., by aggregation.

Solid Feces

For solid feces, the particle division mechanism and the forces at work are the same. Probably, at first the dispersion and the in-depth expansion might seem more burdensome, however also other factors should be considered: being drier, solid feces meet lesser friction and are more easily separable. During dispersion fecal particles are also subjected to drying, yielding most of the moistness thereof. This concept holds true for all cases and situations of fecal particulation. The drier fecal particles are also less absorbed and bound by the clay granules, therefore, for the elimination of feces, besides the clotting the possibility of a particle fraction admixing to the clay granule mass, mingling to the clay flocculate without clotting should also be considered.

These particles, upon admixture to the clay, will totally be inactivated and voided of any enzymatic injuriousness and noxiousness thereby, always remaining coated by clay dust, making the environment surrounding the infant skin clean, sanitized, and healthy at all times.

It has to be specified that one among the several properties of clay is that of sanitizing the environment, blocking bacterial development. Therefore, the granulated clay should mandatorily be in direct contact with the infant skin, since, besides being crucial in dividing the feces, it also provides other properties and capacities, like a health defense, hygiene and cleanliness. According to the present invention, all this is provided by a suitable fabric web 5. Hence, having eliminated and inactivated the various injurious fecal and urine factors, the infant body and skin remains unscathed.

Moreover, the particular arrangement of the pad 3 and 4 enables to use the proper and limited quantity of material, allowing the implementation of lighter-weighted garments. In fact, just a small area is provided for the elimination of the urine, leaving the rest of the garment clean and dry. The dimensions thereof and the quantity of clay depend on the infant age.

Moreover, at worst, in case of any urine leakage, the fraction leaked from its own local area would be absorbed by the adjacent clay-provided areas, thus ensuring the garment to be dry, clean and hygienic at all times.

Figure 2:
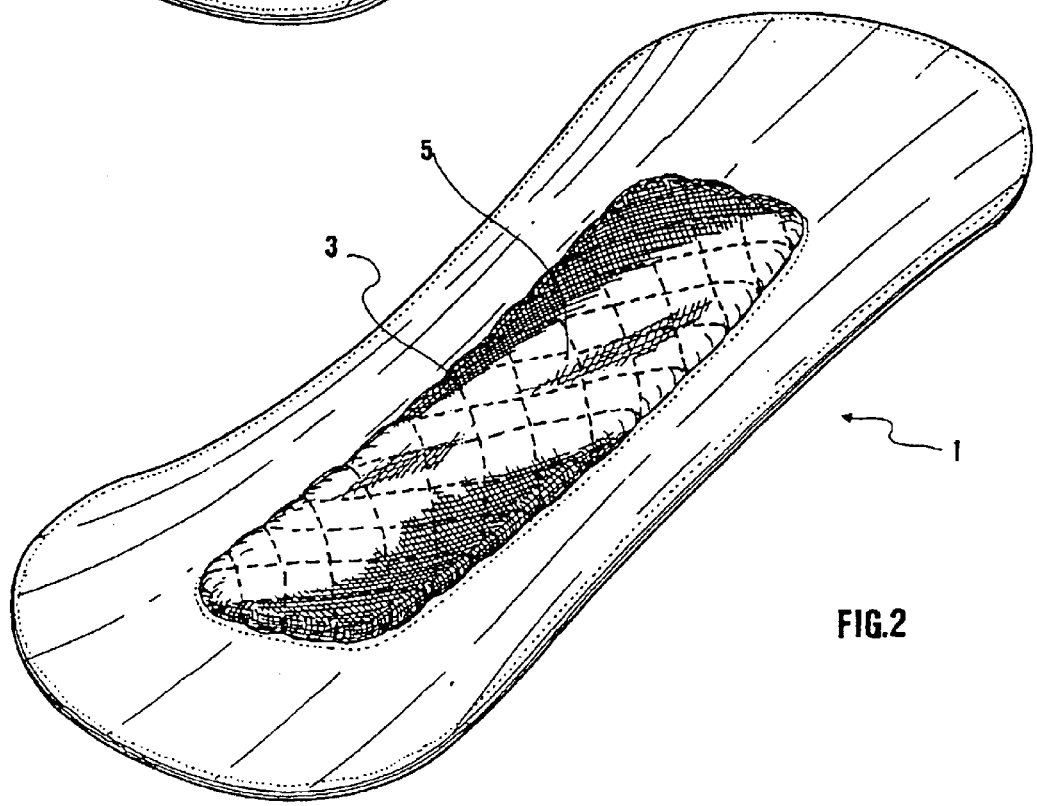
FIG. 2 shows a sanitary absorbent product obtained according to a second embodiment of the present invention.

Making now reference to FIG. 2, an incontinence pad for the aged according to a second embodiment of the present invention is illustrated.

The pad 1 is made of two overlapping pad 3 and 4, respectively, thus implementing a fabric as aboveillustrated with reference to FIG. 5. The urine pad 4 will be the most relevant portion as to the dimension and quantity of clay, and in function of the urine quantity and of the fluidity thereof. The dimensions of the body fluid pad 4 may be of about 5×20 cm. The quantity of granulated clay is set at about 100 gr., and the granulation thereof equals that of the infant diapers. For the solid particles the dimensions of the pad 3 provided with a fabric web 5 will equal those of the pad 4, and the quantity of clay is set at about 70 gr.

Then, the solid particle pad 3 thus manufactured is overlapped to the body fluid pad 4. The former retains a fraction of the liquids and all the biodegraded solid organic particles and the physiological exudates. The joint 2-pad structure forms a diaper 1 ideal for the aged.

The two pads 3 and 4 thus arranged do not have dimensions and thicknesses exceeding those of a conventional sanitary napkin for aged people.

Figure 3:
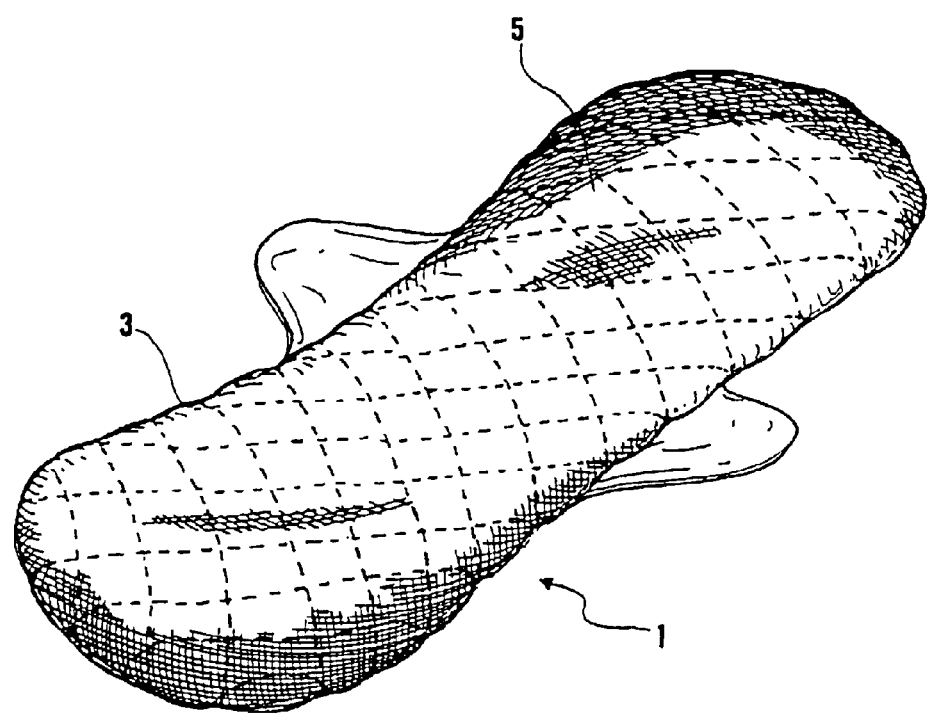
FIG. 3 shows a sanitary absorbent product obtained according to a third embodiment of the present invention.

Making now reference to FIG. 3, a napkin for ladies manufactured according to a third embodiment of the present invention is shown.

In general, the napkin is a simpler sanitary item as there is no large quantity of liquid and solid materials, the issue rather being one of hygiene and cleanliness, due to physiological discharges.

Specifically, in order to provide maximum hygiene and comfort and to attain a less bulky, thinner and easy-fitting product, both in dimensions and in operation, an individual pad web 3 amply suffices to ensure to the organism via the clay-skin contact all of the required defensive and hygienic potential it requires. In this case, the diaper 1 is substantially made of a support web 2 with some clay as absorbing and sanitizing material. The dimensions of the pad 3 are 3×15 cm., and the quantity of clay 30–50 gr. On the other hand, the clay granulometry is <1 mm.

Also for this product thus made the operational quality, the practicality, the hygiene and the overall clean condition are ensured.

Figure 4:
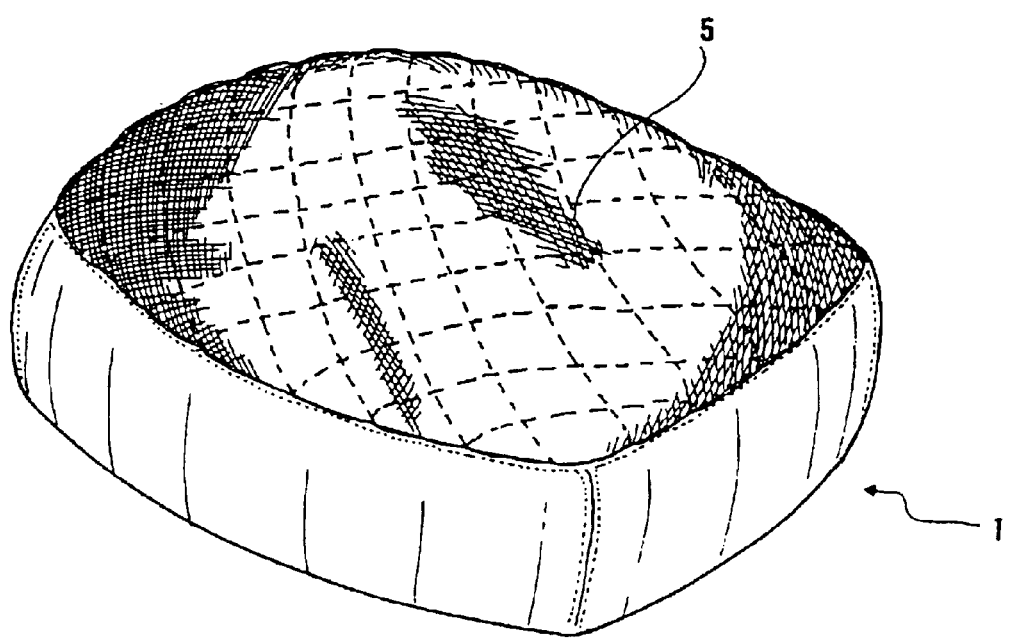
FIG. 4 shows a sanitary absorbent product obtained according to a fourth embodiment of the present invention.

With reference now to FIG. 4, an antibedsore pad according to a fourth embodiment of the present invention is illustrated.

Also in this case the system with two clay-filled bands or pads 3 and 4, the bottom one 4 being shrouded by a plain fabric, the top one 3 being shrouded by a fabric web 5, proved advisable. The two pads 3 and 4 have dimensions alike therebetween, of about 40×40 cm.

In the antibedsore pad case there are no liquids, merely moistness, therefore the aim thereof is that of trying to maintain by natural means a sensitive and drier skin. The role of the bottom portion, or bottom pad 4, will be that of softening the weight, hence it should work as an elastic spring, capable of sealing off the body from the mattress avoiding local overheating and concomitantly generating some airing. The top portion (or pad 3) in contact with the body has both a protective and a sanitizing function, restoring the skin elasticity and strength, remineralizing and mending the tissues, particularly the skin.

The quantity of clay is greater in the bottom pad 4, since it should bear the weight, whereas a smaller quantity of product suffices for the top pad web 3 in order to provide the defensive, curative properties of the clay. The environment thus obtained will be sanitized, dry and clean.

It has to be pointed out that, with the same inventive principles of the aboveillustrated alternative embodiments, a diaper for the physically impaired may be implemented. Therefor, it suffices to suitably resize the infant diaper, increasing the clay quantity therein.

Thus, the urine absorption and elimination in the specific band is ensured, whereas a feces elimination requires a work generated by the body-legs motion. Since for the physically impaired such a body-legs motion is partial, in this case the outcome of the dispersion will be incomplete, being however far superior to that of the marketed conventional diapers.

Moreover, the present invention also applies to the field of plasters, in which the conventional fibrous material portion is replaced by a finely granulated clay, particularly indicated for small wounds and when an absorption of small quantities of biological fluids (pus), etc. is required.

Several examples, with experimental data yielded by wearing tests on infants will hereinafter be provided.

For the direct testing on infants, the present Inventor prepared two sets of diapers, made as in the embodiment disclosed in FIG. 2 and with two fabric web 5 of different size for the feces band (pad 3). The first diaper set had a <1 mm mesh fabric web 5 of the <<sweet-box tulle>> kind, whereas the second diaper set had a ~2 mm mesh fabric web.

For the urine band (pad 4) the preparation was identical for both sets. The present Inventor varied the quantity of clay in the feces band (pad 3) in order to assess the importance of the former; a ~4 mm Ø granulation was adopted in all tests. The band 3 and 4 were adjoined and overlapped onto a fibrous support, like a testing pad. A plastic sheet was inserted between the bands and the cloth in order to seal off the two portions, avoiding any contact therebetween.

To use a natural clay the "green illite" clay was selected, produced in compliance to the ISO norms and having the following composition:

| ELEMENT | % by weight |
|---|---|
| Silica ($SiO_2$) | 49.5 ± 2.5 |
| Aluminum ($Al_2O_3$) | 14.0 ± 1.0 |
| Calcium (CaO) | 8.0 ± 1.0 |
| Iron ($Fe_2O_3$) | 5.0 ± 1.0 |
| Potassium ($K_2O$) | 4.0 ± 1.0 |
| Magnesium (MgO) | 2.5 ± 0.5 |
| Sodium ($Na_2O$) | 0.2 ± 0.1 |
| Manganese (MnO) | 0.2 ± 0.1 |
| Phosphorus ($P_2O_5$) | 0.15 ± 0.05 |

Moreover, the selected clay had the following trace elements, expressed in ppm:

| | |
|---|---|
| Copper (Cu) | 20–10 ppm |
| Cobalt (Co) | 15–10 ppm |
| Lithium (Li) | 3–1 ppm |
| Molybdenum (Mo) | <1 ppm |

Then, the tests were conducted on a bottle-fed 7-month baby producing rather solid feces. For the sake of safety, a clay/mineral and vegetal oil-base cream was applied onto the buttock of the subject to avoid possible reddening.

Three different examples of fecal state with the same type of web are reported, representing the three extreme cases of fecal state in everyday reality. The second and the third case were grouped.

EXAMPLE 1

Fluid feces. This case provides the simpler situation. It has to be pointed out that for each test the diaper made as abovementioned was kept on the baby for at least 7–8 h. 8 hours later, i.e., at the moment of change, the following was observed: the feces carried by the liquid flow had been completely dispersed among the clay granules, easily penetrating the web. The urine was absorbed by the urine band. In practice, the feces and urine elimination rate was of almost the 100%.

The condition of thee baby skin was found clean and dry. Moreover, a <<pad test>> with absorbent paper was conducted for assessing the diaper dampness, detecting no dampness nor fecal soiling whatsoever, merely a light coloring.

Hence, for the fluid feces the diaper thus implemented exhibited an elevated efficiency.

EXAMPLE 2

Pasty Feces. The diaper thus implemented was left in contact with the skin of the same subject for 7–8 h. After testing, at the moment of change, the Inventor observed the presence of a small quantity of feces onto the feces band, however the 85–90% thereof had been dispersed and absorbed. The absorption of the feces did not attain the 100% due to the web mesh dimensions, deemed to be too small. Hence, for suchlike feces a wider mesh is advisable.

On the other hand, in this case the urine was found to be absorbed at the 100% of the diaper capacity.

Then, a pad testing was conducted with absorbent paper, and minimal dampness and fecal soiling were found to be absorbed therein. This indicates the diaper to be in an almost dry condition at +8 h. The overall cleanliness was highly satisfactory.

Concomitantly, a similar test with a currently marketed diaper was conducted, further to which fecal absorption and elimination rates differing from the latter diaper, wherein feces as such lie in contact with the baby skin, to the diaper of the present invention, wherein the 85–90% of the feces was absorbed and the skin of the same subject remained clean and dry, was found.

EXAMPLE 3

Extremely dry feces. In this case, the diaper thus manufactured was left in contact with the skin of the subject for about 7 h. Subsequently, the fecal particulation was found to have occurred, whereas, due to the feces resulting too dry, the absorption ratio thereof was of the 70%. A fraction thereof remained in a dry granulated state onto the diaper, yet it had been incorporated in the clay dust. The feces thus incorporated were in a dry state, causing no inconvenience to the skin of the subject, left dry and clean. Also in this case, a concomitant testing was conducted under similar conditions with a marketed diaper, finding out that, with respect to the latter, the diaper of the present invention always provided a far superior performance.

In the examples hereinafter, tests were conducted with diapers made in a 2 mm-mesh fabric web.

EXAMPLE 4

Fluid feces. In this case, with respect to the abovereported examples, the result was markedly superior due to the effectiveness of the web, allowing a more effective fecal seepage. Moreover, the skin/clay interface was much wider. The diaper was left in contact with the subject skin for about 8 h. Subsequently, an pad test was conducted with absorbent paper, finding the latter perfectly clean and dry.

In this situation, the diaper exhibited an almost 100% efficiency.

EXAMPLE 5

Pasty feces. In this case as well, by virtue of the mesh size, the feces were easily dispersed, particulated and adsorbed by the clay granules. The diaper thus manufactured was left in contact with the skin of the subject for about 8 h. Then, a pad testing was conducted with absorbent paper, finding no evidence of dampness or fecal soiling. The overall diaper condition was clean and dry. The urine was 100% eliminated Concomitantly, a testing was conducted under similar conditions with a currently marketed diaper, and a marked difference in the absorption and presence of feces therein with respect to that of the present invention was found.

EXAMPLE 6

Extremely dry feces. In this case the diaper, having a 2 mm-mesh fabric web, exhibited a greater ease of dispersion for a larger (approx. +50%) quantity of feces. The feces left over were found in a granular and clay-admixed condition, transformed in an innocuous, dry and sanitized mass. The pad test with absorbent paper proved the subject skin to be dry and clean even after approximately 8 h of contact.

Further to such experimental tests, the Inventor observed the diapers according to the present invention to be excellent and qualitatively valid in answering to any physiological need of infants. Moreover, it was found that the diapers manufactured according to present invention provide high quality, properties and functionality with an operational efficiency of the 80–90% of the capacity thereof. Moreover, it was found that the diapers thus manufactured also have a marked deodorant power, by virtue of the clay being capable of absorbing even a gaseous fraction of the body fluids.

It has to be pointed out that the clay utilized in the abovementioned tests was sterilized, not chemically treated natural clay.

What is claimed is:

1. An absorbent product (1) comprising a flexible support (2), a first layer (4) and a second layer (3) of granulated clay material, and a porous fibrous fabric (5) apt to secure said first and second layer (3,4) on said flexible support (2) being arranged at the top thereof, characterized in that said first layer (4) and said second layer (3) are made of porous granulated clays of a granulometry differing therebetween.

2. The absorbent product according to claim 1, wherein said granulometry is $\leq 5$ mm.

3. The absorbent product according to claim 1 or 2, wherein said absorbent product is a diaper (1) for infants.

4. (Original) The absorbent product according to claim 1 or 2, wherein said absorbent product is a diaper (1) for aged people.

5. The absorbent product according to claim 1 or 2, wherein said absorbent product is a sanitary napkin (1) for ladies.

6. The absorbent product according to claim 1 or 2, wherein said absorbent product is an antibedsore pad (1).

7. The absorbent product according to claim 3, wherein said absorbent product is a diaper (1) for infants and wherein said first layer (4) and said second layer (3) are arranged side to side on said flexible support (2).

8. The absorbent product according to claim 1, wherein said first layer (4) and said second layer (3) are arranged overlapped therebetween on said flexible support (2).

* * * * *